United States Patent [19]

Surmatis

[11] 3,932,485

[45] Jan. 13, 1976

[54] PREPARATION OF WITTIG SALT OF VINYL β-IONOL

[75] Inventor: Joseph Donald Surmatis, West Caldwell, N.J.

[73] Assignee: Hoffmann-La Roche Inc., Nutley, N.J.

[22] Filed: Aug. 28, 1974

[21] Appl. No.: 501,127

[52] U.S. Cl. ...... 260/468 L; 260/488 A; 260/551 P; 260/606.5 F; 260/617 A
[51] Int. Cl.$^2$............................................ C07C 67/00
[58] Field of Search .... 260/293.63, 488 A, 606.5 F, 260/617 A, 468 L, 551 P

[56] References Cited
UNITED STATES PATENTS 3,311,656   3/1967   Surmatis .......................... 260/488 A
3,373,207   3/1968   Nuerrenbach et al ........ 260/606.5 F
3,694,491   9/1972   Surmatis .......................... 260/488 A

FOREIGN PATENTS OR APPLICATIONS 1,059,900   6/1959   Germany ......................... 260/488 A Primary Examiner—Sherman D. Winters
Attorney, Agent, or Firm—Samuel L. Welt; Jon S. Saxe; William H. Epstein

[57] ABSTRACT

Improved preparation of Wittig salts of alpha,beta-unsaturated alcohols by treating the alcohol with a phosphine in a basic medium and in the presence of a salt of a weak organic base with a strong acid. The Wittig salt may be reacted further with an unsaturated aldehyde to form a polyene compound.

6 Claims, No Drawings

PREPARATION OF WITTIG SALT OF VINYL β-IONOL

BACKGROUND OF THE INVENTION

This invention relates to an improved preparation of Wittig salts of alpha,beta-unsaturated alcohols. The Wittig salts are useful intermediates for synthesizing polyene compounds, such as vitamin A.

Wittig salts of alpha,beta-unsaturated alcohols have heretofore been prepared by treating the alcohol with a phosphine salt of a strong mineral acid, such as hydrochloric acid. See, for example, German Patent No. 1,059,900. Such preparations of Wittig salts have not however been entirely satisfactory. The use of strong acid salts under acidic conditions and in the presence of an unsaturated aldehyde has been found to cause alpha,beta-unsaturated alcohols to dehydrate and/or rearrange. As a consequence, the yields of Wittig salts from such processes have been relatively low due to the formation of dehydration and/or rearrangement by-products.

The formation of by-products has been a particularly severe problem in preparing Wittig salts of tertiary alcohols, wherein the hydroxy group is quite labile and the alcohol is hence quite prone to undergo rearrangement and/or dehydration. In this regard, it has been found that by utilizing, the process disclosed in German Patent No. 1,059,900, the yield of the Wittig salt of vinyl-beta-ionol has been quite low. This means that the overall process furnishes an improved polyene end-product with regard to purity and yield.

There has been an unfilled need therefore for an improved method of producing Wittig salts of alpha,-beta-unsaturated alcohols.

SUMMARY OF THE INVENTION

In accordance with the process of this application, Wittig salt of alpha,beta-unsaturated alcohols are produced by treating the alcohol with a phosphine of the formula:

wherein
R₁ is alkyl, aryl, aryl lower alkyl, di(lower alkyl)amino, piperidinyl or pyrrolidinyl; and R₂ and R₃ are lower alkyl, aryl, aryl lower alkyl, di(lower alkyl)amino, piperidinyl or pyrrolidinyl;

in a basic medium and in the presence of a salt of a weak organic base with a strong acid. The phosphonium salt formed may be reacted with an unsaturated aldehyde to yield a polyene compound.

DETAILED DESCRIPTION OF THE INVENTION

As used throughout this application, the term "alpha,beta-unsaturated alcohol" comprehends any primary, secondary or tertiary, alpha-beta-unsaturated alcohol which can rearrange to form an alpha-beta-unsaturated Wittig salt. Among the alpha,beta-unsaturated alcohols of this invention are the alcohols of the formula:

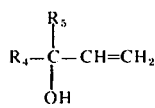       II wherein
R₄ is Δ¹⁽²⁾-lower alkenyl or Δ¹⁽²⁾-lower alkenyl substituted with nitrile, cyclo lower alkyl, cyclo lower alkenyl, cyclo lower alkoxy, cyclo lower alkenyloxy or aryl; and R₅ is hydrogen, lower alkyl, lower alkenyl, cyclo lower alkyl or cyclo lower alkenyl.

Among the preferred alpha,beta-unsaturated alcohols of formula II are the compounds of the formula:

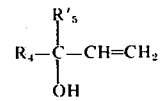       II-A wherein
R₄ is as in formula II above and R'₅ is lower alkyl or lower alkenyl.

Among the alpha,beta-unsaturated alcohols of formula II-A, preferred are the alcohols of the formula:

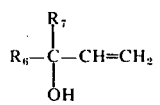       II-B wherein
R₆ is Δ¹⁽²⁾-lower alkenyl substituted with cyclo lower alkyl or cyclo lower alkenyl and R₇ is lower alkyl.

The particularly preferred alpha,beta-unsaturated alcohols are compounds of the formulae:

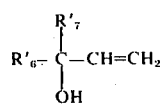       II-C wherein
R'₆ is cyclo lower alkenyl lower alkenyl; and R'₇ is methyl;

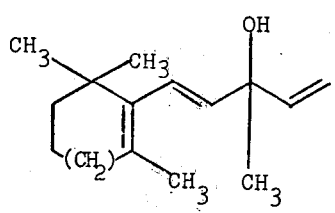       II-D wherein
n is a whole integer from 0 to 2.

and

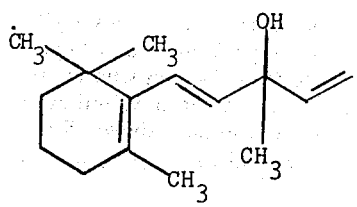       II-E

As also used throughout this specification, the term "alkyl" comprehends straight chain and branched chain, saturated aliphatic hydrocarbon groups of 1 to 12 carbon atoms. Where the alkyl group of this application is substituted, this group may be substituted with one or more groups such as lower alkoxy, lower alkenyloxy, hydroxy, oxo, nitro, nitrile, cyclo lower alkyl, cyclo lower alkenyl, cyclo lower alkoxy, cyclo lower alkenyloxy, and aryl groups. Also in this specification, the term "lower alkyl" comprehends alkyl groups of 1 to 6 carbon atoms, such as methyl, ethyl isopropyl and tert-butyl. Where the lower alkyl group is substituted this group may be substituted with one or more of the same substituents defined above with relation to the substitution of alkyl groups.

Also throughout this specification, the term "cyclo lower alkyl" comprehends saturated, aliphatic hydrocarbon groups of 3 to 8 carbon atoms, containing one or more, saturated, mononuclear or polynuclear, cycloaliphatic moieties, such as cyclopropyl and cyclohexyl. Where the cyclo lower alkyl groups of this application are substituted, these groups can be substituted in one or more positions with a lower alkyl, lower alkenyl, lower alkoxy, lower alkenyloxy, hydroxy, oxo, nitro or nitrile substituent.

As further used throughout this application, the term "lower alkenyl" comprehends straight chain and branched chain, aliphatic hydrocarbon groups of 2 to 7 carbon atoms which contain one or more, olefinic double bonds. Where the alkenyl groups of this application are substituted, these groups can be substituted with one or more groups, such as nitrile, cyclo lower alkyl, cyclo lower alkenyl, cyclo lower alkoxy, cyclo lower alkenyloxy, and aryl groups.

Further throughout this specification, the term "cyclo lower alkenyl" comprehends aliphatic hydrocarbon groups of 3 to 8 carbon atoms containing one or more, mononuclear or polynuclear, cycloaliphatic moieties, of 3 to 8 carbon atoms, with at least one of the cycloaliphatic moieties containing one or more, olefinic double bonds, such as cyclohexenyl. The cycloalkenyl groups of this application may be unsubstituted or substituted in one or more positions with a lower alkyl, lower alkenyl, lower alkynyl, lower alkoxy, lower alkenyloxy, lower alkynyloxy, hydroxy, oxo, nitro or nitrile substituent.

As still further used throughout this specification, the term "alkynyl" comprehends straight chain and branched chain, aliphatic hydrocarbon groups of 2 to 20 carbon atoms which contain one or more, acetylenic triple bonds. The alkynyl group of this application can be unsubstituted or substituted with one or more groups, such as alkoxy, alkenyloxy, alkynyloxy, alkyl, alkenyl, hydroxy, oxo, nitro, nitrile, cycloalkyl, cycloalkenyl, cycloalkynyl, cycloalkoxy, cycloalkenyloxy, cycloalkynyloxy and aryl groups. Still further in this application, the term "lower alkynyl" comprehends alkynyl groups of 2 to 6 carbon atoms, such as ethynyl, 1-propynyl, penta-2,5-diynyl, and hex-2-en-5-ynyl.

Further herein, the terms, "lower alkoxy", "lower alkenyloxy", "cyclo lower alkoxy" and "cyclo lower alkenyloxy" comprehend the groups wherein the lower alkyl, lower alkenyl, cyclo lower alkyl and cyclo lower alkenyl moieties are as defined above. Still further herein, the terms "aryl lower alkyl" and "di(lower alkyl)amino" comprehend groups wherein the lower alkyl and aryl moieties are as defined above.

The term "esterified —CH$_2$OH group" encompasses a group of the formula:

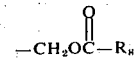

wherein

R$_8$ is lower alkyl, aryl or aryl lower alkyl.

A preferred lower alkyl group is the methyl group and a preferred aryl group is the phenyl group. The benzyl group is the preferred aryl lower alkyl group.

The term "etherified —CH$_2$OH group" encompasses a group of the formula:

—CH$_2$OR$_9$ wherein

R$_9$ is lower alkyl, aryl, aryl lower alkyl or tetrahydropyranyl.

Again a preferred lower alkyl group is the methyl group, a preferred aryl group is the phenyl group and a preferred aryl lower alkyl group is the benzyl group.

Still further herein, the term weak organic base comprehends any conventional organic base having a pK value of 10$^{-8}$ or less. Among the preferred organic bases are the primary and secondary amine bases, such as the mono and di-lower alkyl amine bases and the cyclic amines. The particularly preferred, weak organic bases include those having a pK value of 10$^{-8}$ to 10$^{-12}$, especially bases such as aniline, alpha-napthylamine, diethyl aniline, p-phenetidine, o-phenylenediamine, p-phenylenediamine, pyridine, quinoline and toluidine, quite especially pyridine.

Further herein, the term "basic medium" encompasses a reaction medium the pH of which is in the range of about 7.5 to about 11, preferably of about 8 to about 10.

Also herein, the term "strong acid" comprehends any conventional strong acid which can form an acid addition salt with the phosphines of formula I. Among the conventional strong acids are the acids disclosed in U.S. Pat. No. 3,441,623, column 4, lines 62 to 70, such as the strong, inorganic acids, e.g., HCl, HBr, HI, and H$_2$SO$_4$, and the strong organic acids, e.g., benzenesulfonic acid and trichloroacetic acid. The preferred strong acid is HCl.

In accordance with this invention, a Wittig salt of an alpha,beta-unsaturated alcohol can be expeditiously obtained by treating the alcohol of formula II with the phosphine of formula I in the presence of a salt of a weak organic base with a strong acid in an inert organic solvent. The medium utilized in this reaction has to be basic, the pH being in the range from about 7.5 to about 11, preferably from about 8 to about 10. The basic medium is provided by using an excess of a base, preferably the weak organic base which is a component in the formation of the salt of a weak organic base with a strong acid mentioned hereinbefore. This reaction takes place in an inert organic solvent medium. Any of the inert organic solvents conventionally utilized in the Wittig synthesis can be utilized in the reaction medium. Among the preferred conventional inert organic solvents which form the reaction medium are the solvents disclosed in U.S. Pat. No. 3,441,623, column 4, lines 60 to 62, such as the lower alkanols, e.g., methanol and ethanol, the aromatic hydrocarbons, e.g., benzene and toluene, the chlorinated hydrocarbons, e.g., methylene chloride and chloroform, and the ethers, e.g., tetrahydrofuran, dioxane and diethyl ether.

In carrying out this reaction, temperature and pressure are not critical, and any temperature between 0°C. and the reflux temperature of the reaction mixture can be suitably utilized. Preferably, this reaction is carried out at about 20°C. to 30°C.

Also in this process, the ratio of reactants is not critical. Preferably, from 1 to 10 moles of the alpha, beta-unsaturated alcohol of formula II and 1 to 10 moles of the phosphine of formula I are utilized in the presence of 1 to 10 moles of the salt of the weak organic base with a strong acid. It is particularly preferred that about equal molar part of the phosphine, alcohol and salt be utilized.

By the process of this application, improved yields of Wittig salt of alpha, beta-unsaturated alcohols can be obtained, with decreased amounts of polyene hydrocarbon by-products.

The phosphonium salt obtained as described herein before may be reacted with an unsaturated aldehyde of the formula III:

$$OHC-\underset{\underset{CH_3}{|}}{C}=CH-X \qquad III$$

wherein
X is a —CH$_2$OH group, an esterified or etherified —CH$_2$OH group, a —COOH group, a —CH$_2$N(lower alkyl)$_2$ group or a lower alkyl group;

to form a corresponding polyene compound. Therefore the two step process for the preparation of polyene compounds comprises reacting (a) an alpha,beta-unsaturated alcohol with a phosphine of the formula:

$$R_3-\underset{\underset{R_1}{|}}{\overset{\overset{R_2}{|}}{P}}-R_1 \qquad I$$

wherein
R$_1$ is alkyl, aryl, aryl lower alkyl, di(lower alkyl)amino, piperidinyl or pyrrolidinyl; and R$_2$ and R$_3$ are lower alkyl, aryl, aryl lower alkyl, di(lower alkyl)amino, piperidinyl or pyrrolidinyl;

in a basic medium and in the presence of a salt of a weak organic base with a strong acid to form a phosphonium salt of said unsaturated alcohol and (b) condensing said phosphonium salt obtained with an unsaturated aldehyde of the formula III. The phosphonium salt formed in reaction step (a) may be isolated or may be reacted directly in the reaction medium where it is formed with the unsaturated aldehyde. The condensation of the phosphonium salt with the unsaturated aldehyde is conducted in the presence of a proton acceptor. The proton acceptors employed are preferably basic agents, e.g., strong bases such as alkali metal hydroxides, alkaline earth metal hydroxides, alkali metal amides, alkaline earth metal amides, alkali metal alcoholates, alkaline earth metal alcoholates, ammonia, strongly basic amines, metalloorganic compounds, particularly Group I metallo-alkyl and Group I metallo aryl compounds, such as lithium methyl, lithium phenyl, sodium phenyl, sodium methyl, Grignard compounds, e.g., alkyl and aryl magnesium halides, etc. Sodium methoxide and potassium hydroxide are preferred although sodium amide has been found quite effective.

The temperature of this reaction is not critical and room temperature can be utilized. Generally, it is preferred to carry out this condensation reaction at a temperature of from −50°C. to +40°C. Furthermore, it is generally preferred to carry out this condensation reaction in the presence of an inert organic solvent. The preferred solvents employed in this reaction are methanol, tetrahydrofuran, pyridine, isopropyl ether, isopropanol and ethyl ether, although any inert solvent may be employed.

Preferred unsaturated aldehydes are compounds of the following formulae:

$$OHC-\underset{\underset{CH_3}{|}}{C}=CH-COOH;$$

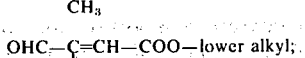

$$OHC-\underset{\underset{CH_3}{|}}{C}=CH-COO-\text{lower alkyl};$$

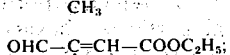

$$OHC-\underset{\underset{CH_3}{|}}{C}=CH-COOC_2H_5;$$

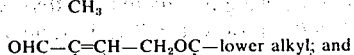

$$OHC-\underset{\underset{CH_3}{|}}{C}=CH-CH_2O\underset{\underset{O}{\|}}{C}-\text{lower alkyl; and}$$

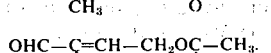

$$OHC-\underset{\underset{CH_3}{|}}{C}=CH-CH_2O\underset{\underset{O}{\|}}{C}-CH_3.$$

The examples which follow further illustrate the process of this invention. Unless otherwise stated all temperatures are in degrees C.

EXAMPLE 1

In a two-liter flask fitted with a stirrer, thermometer condenser, and nitrogen inlet, there were placed 1,125 ml. of methyl alcohol, 25 ml. of pyridine, 25 ml. of concentrated hydrochloric acid and 2 ml. of 10% by wt. Butylated Hydroxy Anisole solution in benzene. The solution was stirred for 5 min., and 70 g. of triphenylphosphine and 60 g. of vinyl-β-ionol (92.2% pure) were added all at once. The reaction mixture was heated to boiling and stirred at the reflux temperature of methyl alcohol for 30 min. At the end of this period, an analysis by thin layer chromatography showed that the reaction was completed. The solvent was removed under vacuum and the remaining residue was stirred with 1,000 ml. of ethyl acetate, to which a few crystals of β-ionylidenethyl-triphenylphosphonium chloride were added. The solvent was again removed under vacuum, and the crystalline solid remaining in the phase was stirred with 650 ml. of ethyl acetate and cooled in a refrigerator overnight. The crystalline solid was filtered, washed with two 50 ml. portions of ethyl acetate (10°C.) and dried in vacuum oven at 45°–50°C. Obtained was 120.4 g. (96%) of β-ionylidenethyl-triphenylphosphonium chloride.

EXAMPLE 2

In a 5-liter reaction flask, there were placed 2,250 ml of methyl alcohol, 4 ml. of 10% butylated hydroxy anisole solution in benzene, 50 ml. of pyridine and 50 ml. of concentrated hydrochloric acid. The solution was stirred for 5 min., and 139 grams of triphenylphosphine and 120 g. (92.2% pure) of vinyl-β-ionol were added all at once. The mixture was stirred under an atmosphere of nitrogen for 24 hr.

The reaction mixture was washed with 2,000 ml. of hexane, then with two 1,000 ml. portions of hexane. The alcoholic layer was separated, and the solvent was removed under vacuum.

The resulting residue, consisting mainly of β-ionylidenethyl-triphenylphosphonium chloride was dissolved in 2,000 ml. of isopropyl alcohol and placed in a three-liter flask with 10 ml. of a 10% by wt. solution of butylated hydroxy anisole in benzene. The solution was cooled to −35°C. Then 84 g. (90% purity) of γ-acetoxytiglicaldehyde was placed in the reaction flask and a solution consisting of 42.5 g. ( % pure) potassium hydroxide in 42 ml. of water was dropped into the stirred reaction in 15 min. The reaction mixture was then stirred at −35°C. for an additional 30 min.

The reaction mixture was poured into a separator with 3 liters of water and 2 liters of hexane. The oil layer was separated and the aqueous portion was extracted with four 500 ml. portions of hexane. The combined oil extracts were washed with four 500 ml. portions of 80% by weight aqueous methyl alcohol and then with 1,000 ml. of water. The hexane solution was dried over anhydrous sodium sulfate, and the solvent was removed under vacuum. The yield of vitamin A acetate was 153 g. (93% based on vinyl-β- ionol).

I claim:

1. A process for preparing a phosphonium salt comprising reacting an alpha, beta-unsaturated alcohol of the formula:

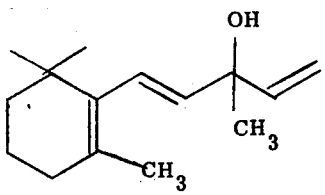

with a phosphine of the formula:

wherein $R_1$ is alkyl of from 1 to 12 carbon atoms, phenyl, phenyl lower alkyl or di(lower alkyl) amino wherein lower alkyl contains from 1 to 6 carbon atoms; and $R_2$ and $R_3$ are lower alkyl, phenyl, phenyl lower alkyl or di (lower alkyl) amino wherein lower alkyl contains from 1 to 6 carbon atoms in a basic medium and in the presence of a salt of a weak organic base with a strong acid.

2. A process for the preparation of polyene compounds comprising reacting an alpha, beta-unsaturated alcohol:

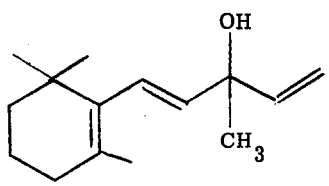

with a phosphine of the formula:

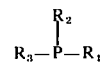

wherein $R_1$ is alkyl of from 1 to 12 carbon atoms, phenyl, phenyl lower alkyl or di(lower alkyl) amino wherein lower alkyl contains from 1 to 6 carbon atoms; and $R_2$ and $R_3$ are lower alkyl, phenyl, phenyl lower alkyl or di (lower alkyl) amino wherein lower alkyl contains from 1 to 6 carbon atoms in a basic medium and in the presence of a salt of a weak organic base with a strong acid to form a phosphonium salt of said unsaturated alcohol and condensing said phosphonium salt obtained with an unsaturated aldehyde of the formula:

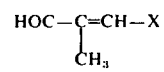

wherein X is

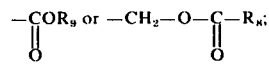

and $R_8$ and $R_9$ are lower alkyl of from 1 to 6 carbon atoms.

3. The process according to claim 1 wherein said basic medium has a pH value in the range of 7.5 to about 11.

4. The process according to claim 2 wherein said basic medium has a pH value in the range of about 7.5 to 11.

5. The process of claim 2 wherein said unsaturated aldehyde is a compound of the formula:

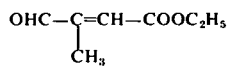

6. The process of claim 2 wherein said unsaturated aldlehyde is a compound of the formula;

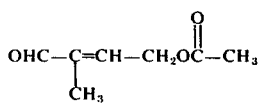

* * * * *